United States Patent [19]
Williams et al.

[11] Patent Number: 6,060,474
[45] Date of Patent: May 9, 2000

[54] METHOD FOR PREVENTING SCAR TISSUE FORMATION

[75] Inventors: Riley J. Williams, New York, N.Y.; Jo A. Hannafin, Greenwich, Conn.

[73] Assignee: New York Society for the Relief of the Ruptured and Crippled Maintaining the Hospital for Special Surgery, New York, N.Y.

[21] Appl. No.: 09/186,452

[22] Filed: Nov. 5, 1998

[51] Int. Cl.$^7$ .............................. A61K 31/495; A61K 9/22
[52] U.S. Cl. ......................... 514/253; 514/254; 604/891.1
[58] Field of Search ...................................... 514/254, 253, 514/891.1; 604/891.1

[56] References Cited

PUBLICATIONS de la Garza, Achilles Tendon Rupture and Fluoroquinolones Use: Report of Two Cases, Arch. Med. Res., ,28, 429–30 (1997).

Movin et al., Pathology of Achilles Tendon in Association with Ciprofloxacin Treatment, Foot & Ankle International, 18, 297–99 (1997).

Moreira et al., Effect of Topical Fluoroquinolones on Corneal Re–Epithelialization After Excimer Laser Keratectomy, J. Cataract Refract. Surg. 23, 845–48 (1997).

McGarvey et al., Partial Achilles Tendon Ruptures Associated with Fluoroquinolone Antibiotics: A Case Report and Literature Review, Foot & Ankle International 17, 496–98 (1996).

Zabraniecki et al., Fluoroquinolone Induced Tendinopathy: Report of 6 Cases, J. Rheumatol. 23, 516–20 (1996).

Szarfman et al., More on Fluoroquinolone Antibiotics and Tendon Rupture, N. Eng. J. Med., 332, 193 (1995).

MacGowan et al., Serum Ciprofloxacin Concentrations in Patients with Severe Sepsis Being Treated with Ciprofloxacin 200 MG IV BD Irrespective of Renal Function, Journal of Antimicrobial Chemotherapy, 33, 1051–54 (1994).

Royer et al., Features of Tendon Disorders with Fluoroquinolones, Therapie 49, 75–76 (1994).

Shah et al., Comparative Pharmocokinetics and Safety of Ciprofloxacin 400 MG IV Thrice Daily Versus 750 MG PO Twice Daily, Journal of Antimicrobial Chemotherapy, 33, 795–801 (1994).

Lee, J. Ciprofloxacin Associated Bilateral Achilles Tendon Rupture, Aust. N.Z. J. Med. 22, 500 (1992).

Bergeron, The Pharmacokinetics and Tissue Penetration of the Fluoroquinolones, Clin. Invest. Med. 12, 20–27 (1989).

Crump et al., Pharmacokinetics and Tissue Penetration of Ciprofloxacin, Antimicrob. Agents Chemother. 24, 784–86 (1983).

*Primary Examiner*—Elli Peselev
*Attorney, Agent, or Firm*—Darby & Darby

[57] ABSTRACT

Disclosed herein are methods for reducing or preventing scar tissue formation by administering an antifibrotic amount of a fluoroquinolone. Also disclosed are means for inhibiting the activity of fibroblast cells, including their proliferation, metabolism, and invasion into tissue. The invention further contemplates methods and compositions for the delivery of a fluoroquinolone to prevent or treat scar tissue formation, including oral and intravenous delivery means.

21 Claims, No Drawings

METHOD FOR PREVENTING SCAR TISSUE FORMATION

FIELD OF THE INVENTION

This invention relates to methods for inhibiting fibrosis, fibroblast proliferation, matrix synthesis, joint capsule contracture, collagen synthesis, fibroblast proteoglycan synthesis, promoting fibroblast protease synthesis, treating adhesive capsulitis (frozen shoulder), and for treating wounds and attendant complications, such as scar formation and surgical adhesions, using fluoroquinolone antibiotic agents.

BACKGROUND OF THE INVENTION

Fibroblast cells are particularly important in the wound healing process and in the aging of the skin. Hyperplasia and proliferation of soft tissue fibroblasts are vital to normal healing mechanisms. However, in some cases, an exaggerated healing response can result in the production of copious amounts of healing tissue (ground substance), also termed scar tissue. For example, various traumatic incidents, such as burns, surgery, infection and wounds are often characterized by the erratic accumulation of fibrous tissue rich in collagen and having increased proteoglycan ("PG") content. In addition to the replacement of normal tissue which has been damaged or destroyed, excessive and disfiguring deposits of collagen and new tissue sometimes form during the healing process. The excess collagen deposition has been attributed to a disturbance in the balance between matrix synthesis and matrix degradation, resulting from increased fibroblast metabolism and proliferation. Thus, therapies inhibiting fibroblast metabolism and proliferation, deposition of collagen, and formation of new tissue resulting therefrom, would be useful for treating scar tissue formation.

Surgical adhesions are attachments of organs or tissues to each other through scar tissue formation; such adhesions can cause severe clinical problems. The formation of some scar tissue after surgery or tissue injury is normal. In some cases, however, the scar tissue overgrows the region of injury and creates surgical adhesions, which tend to restrict the normal mobility and function of affected body parts. In particular, fibroblast proliferation and matrix synthesis is increased locally following such soft tissue injury. Adhesions then form when the body attempts to repair tissue by inducing a healing response. For example, this healing process can occur between two or more otherwise healthy separate structures (such as between loops of bowel following abdominal surgery). Alternately, following local trauma to a peripheral nerve, fibrous adhesions can form, resulting in severe pain during normal movement. Current measures for treating adhesions include localized surgical implants containing an amount of a compound that must remain present at the wound site to provide scar-reducing benefit. However, implants may induce a foreign body reaction in the host subject, and predispose the implantation site to infection. Thus, it would be beneficial to systemically administer a scar-reducing composition since this would allow greater control with respect to dosage and frequency of administration, and is non-invasive.

Keloids are tumors of connective tissue consisting of hyperplastic masses which occur in the dermis and adjacent subcutaneous tissue, most commonly following trauma, in certain susceptible individuals. Keloid lesions are formed when local skin fibroblasts undergo vigorous hyperplasia and proliferation in response to local stimuli. Known therapies for keloids, such as local injections of corticosteroids, have had only limited success, and scarring frequently recurs after a keloid is surgically removed. It would be beneficial for a patient to receive less invasive treatment of keloids, and to avoid scarring.

Hypertrophic scars are masses which can result from burns or other injuries to the skin. Such scars are usually permanent and resistant to known methods of therapy. It would be beneficial to have a method for successfully treating hypertrophic scars.

Depressed scars resulting from an inflammatory episode are characterized by contractions of the skin, and leave a cosmetically displeasing and permanent scar. The most common example is scarring which occurs following inflammatory acne. The depression occurs as a normal consequence of wound healing, and the scar tissue causing the depression is predominantly comprised of collagen resulting from fibroblast proliferation and metabolism. Some acne patients are successfully treated using steroids injected intralesionally, topical liquid nitrogen applications, or dermabrasion. In many cases, however, there is either no improvement or the treatment results in other complications. Additional disfiguring conditions of the skin, such as wrinkling, cellulite formation and neoplastic fibrosis also appear to result from excessive collagen deposition, which produces unwanted binding and distortion of normal tissue architecture. Collagenase, an enzyme which degrades collagen, has been injected intralesionally to reduce scarring in these conditions. However, multiple disfigurements may arise, which make local treatments difficult or impossible. Thus, it would be beneficial to provide patients with systemic treatments that could target conditions that are diffuse or not localized.

Proper wound healing generally requires restoration of the integrity of skin, tissue, or organ by use of sutures, staples and/or various adhesive closures. To promote wound healing, topical preparations of oil soluble vitamins such as Vitamin A, D, and E have been applied, but the efficacy of these treatments has not been established by controlled clinical studies.

Other treatments exist to promote wound healing and thereby decrease scarring through anti-fibrotic activity (i.e., by having an inhibitory effect upon fibrosis), including administration of collagenase, para-amino benzoic acid, dextran sulfate, and cross-linked hyaluronic acid. U.S. Pat. No. 5,731,298 describes a pharmaceutical composition for non-topical wound, scar and keloid treatment which contains cross-linked glycosaminoglycans. However, the pharmaceutical composition is administered intralesionally, i.e., by injection into the site where scar-reducing activity is desired. U.S. Pat. No. 4,524,065 describes a method in which collagenase is injected intralesionally to cleave bonds in the collagen structure comprising the scar, thereby permitting other enzymes to act on the resulting molecular fragments and reduce the scar tissue. U.S. Pat. No. 5,705,177 describes a method of using anionic polymers such as dextran sulfate and pentosan polysulfate to inhibit fibrosis, scar formation, and surgical adhesions. This method is even more invasive than those described above since it requires implantation of a surgical graft that has been treated with the antifibrotic compounds.

Thus, many problems are associated with known treatments for scar tissue. Most treatments require invasive techniques, such as injection, or implantation of a surgical device that releases an antifibrotic compound. Topical administration is less invasive, but requires monitoring since the topical preparation may be accidentally rubbed off or absorbed by a bandage. Furthermore, topical preparations do not reduce scarring beneath the skin, and are therefore ineffective against adhesions. Also, it is difficult to control the tissue concentration and penetration of locally applied drugs.

Known preventative measures generally require a physician to administer the relevant drug to the site of a surgical wound or lesion (e.g., by injection or surgical implant), usually at the time that such wound or lesion would occur. Thus, there is a need for an effective preventive treatment against scarring, and fibrosis generally, that involves less invasive means, and permits more certainty as to the amount of active ingredient reaching the site of the wound or lesion.

In addition, known methods of treatment require that the active ingredient remain at the site of administration for a sufficient time to be effective. But this often does not occur and several invasive administrations are required. Thus, it would be beneficial for the level of active ingredient to be maintained at the site of treatment without additional local administrations.

Also, stiff joints are caused by capsular contractures, adhesive capsulitis, and arthrofibrosis, which result from musculoskeletal surgery. Such stiff joints (e.g., knees, shoulders, elbows, ankles, and hips) inevitably cause abnormally high forces to be transmitted to the articular cartilage of the affected area. Over time, these forces result in the development of degenerative joint disease and arthritis. All of these conditions occur as a result of increased fibroblast matrix synthesis and resultant scar formation. For example, in arthrofibrosis and capsular contracture, fibroblasts form excessive amounts of matrix in response to local trauma, such as joint dislocation. In adhesive capsulitis (frozen shoulder), an excessive inflammatory response results in the unfettered production of cytokines and growth factors. This results in a scarred contracted shoulder capsule and causes joint stiffness.

There is a need in the art for a method of treating conditions such as these that are caused by scar formation.

SUMMARY OF THE INVENTION

The present invention is directed to the use of synthetic antibiotics known as fluoroquinolones for preventing scar tissue formation or treating preexisting scar tissue. The invention relates in part to the discovery that fluoroquinolones effectively inhibit the metabolism, proliferation and invasion of fibroblast cells, i.e., fibrosis, associated with detrimental healing processes, and thus inhibit scarring, adhesion formation, and joint stiffness.

The present invention overcomes shortcomings of the prior art by providing improved methods for promoting the healing of wounds. More particularly, it provides methods for reducing the formation of scar tissue and related pathologies as disclosed herein. The invention differs markedly from other methods of treating wounds and preventing scar tissue formation by providing for the systemic delivery of a fluoroquinolone, such as by oral or intravenous administration. Systemic administration permits a less invasive or noninvasive means for treating a patient susceptible to scar tissue formation or related pathologies. In addition, systemic administration permits a physician to have greater control over drug administration, including frequency and dosage, without concern as to whether, for example, a locally administered drug is effectively releasing active ingredient or whether contents of an injection remain at the desired site.

The improved treatments of the invention exploit the discovery that fluoroquinolones at serum levels found following oral and intravenous dosing have an inhibitory effect on fibroblast metabolism and proliferation, and matrix, collagen, and proteoglycan syntheses. Thus, the invention provides methods for inhibiting fibroblast metabolism, including proliferation and migration, as well as related processes such as collagen, matrix, and PG syntheses, at the site of an injury or other trauma.

The invention further provides methods for treating or preventing the formation of scar tissue and similar conditions that are manifested by the action of fibroblast cells. Thus, the invention treats or prevents fibrosis, keloidosis, fibrocystic conditions, adhesive capsulitis, capsular contracture, arthrofibrosis, and the like.

The invention will be readily understood by consideration of the Detailed Description of the Invention and the claims, and is limited only through the scope of the claims and their equivalents.

DETAILED DESCRIPTION OF THE INVENTION

All patents, patent applications, and publications cited herein are hereby incorporated by reference in their entireties.

The present invention relates to the discovery that a class of synthetic antibiotics known as fluoroquinolones may effectively inhibit scar tissue formation or reduce preexisting scar tissue. More specifically, the invention inhibits fibrosis at the site of a wound or other pathological condition, including inhibition of the metabolism, proliferation, and/or invasion of fibroblast cells, and consequentially, collagen and proteoglycan matrix syntheses. Thus, the invention inhibits the activity of fibroblasts during scar tissue formation. The effect of this action on fibroblast activity is an inhibition of fibrosis at a site where scar tissue should normally form, and thus prevention of scar formation. Therefore, the anti-fibrotic activity of the invention encompasses treatments for preventing or reducing the formation of scar tissue at the site of a wound or lesion in the skin, tissue or organ of an animal. In particular, the invention encompasses, without limitation, treatment of keloidosis, arthrofibrosis, capsular contracture, adhesive capsulitis, scleroderma, skin lesions, surgical adhesions, scar formation, and the like.

Fibrosis is the formation of fibrous tissue as a reparative or reactive process, as opposed to a process for forming a normal constituent of an organ or tissue. To inhibit fibrosis, the present invention inhibits or reduces any of fibroblast proliferation, collagen synthesis, PG and matrix syntheses, and the effects of these processes. Thus, the invention may also inhibit metalloprotease activity and promote caseinolytic activity.

Preferably, the invention is directed to methods of using fluoroquinolones to inhibit, prevent, or regulate fibrosis, fibroblast invasion or migration, and fibroblast metabolism and proliferation, where such activity is desired, including therapeutic uses thereof. The invention is further directed to methods of using one or more antifibrotic fluoroquinolones to inhibit, prevent, or reduce scar tissue formation, adhesions, as well as other fibrotic conditions, including fibrocystic conditions.

Thus, according to the invention, fluoroquinolone drugs are used to treat stiff joints. Since these conditions arise due to the excessive production of matrix substances, prevention of these processes is accomplished by systemic administration of the fluoroquinolone drug. In addition, fluoroquinolones induce matrix metalloprotease production in joint fibroblasts. Administration of the fluoroquinolones makes stiff joint conditions amenable to manipulation or therapy intended to gain additional range of motion. In some cases, surgery otherwise needed to increase range of motion may be avoided. Moreover, for patients who do require such surgery, the fluoroquinolones can be administered to preserve the increase in range of motion that is obtained, e.g., in surgery to release stiff capsular structures.

Preferably, one or more fluoroquinolones are administered according to the invention in oral or I.V. dosages of about 10 mg to about 3,000 mg, one or two times a day. More preferably, one or more fluoroquinolines is administered in a dosage of about 200 to 800 mg, one to three times each day. For oral administration of fluoroquinolones, most preferably dosages are about 250 mg to about 750 mg once or twice a day. For I.V. administration, dosages are most preferably about 200 mg to 400 mg two to three times each day.

The administration of fluoroquinolone according to the invention will preferably result in blood concentrations at the site requiring treatment of about 0.1 µg/ml to about 100 µg/ml. A physician can determine concentrations of fluoroquinolone in the blood based upon the patient's weight, dosage and mode of administration, as described in Physician's Desk Reference. The course of treatment should preferably continue for about 5 to about 45 days, more preferably about 7 to about 14 days. Treatments according to the invention are also preferably carried out for a longer time period than for conventional fluoroquinolone administration used to achieve antibiotic effect. In one embodiment, the fluoroquinolone is administered for a period of greater than 45 days and in another embodiment for more than 90 days.

In one embodiment, fluoroquinolone administration is carried out according to the invention as an adjuvant therapy to an antibiotic therapy. For example, in the prevention of scar tissue associated with surgical procedures, the method of the invention can be carried out in addition to conventional antibiotic therapy, which might be employed to prevent infection resulting from the procedure.

In another embodiment, the fluoroquinolone is administered in a dosage that is substantially greater or less then that employed to treat infection.

In one embodiment, a fluoroquinolone is administered to inhibit scar tissue resulting from a surgical procedure such as a knee, shoulder or hip arthrotomy or implantation of an orthopedic device, in particular by surgical implant such as a knee, hip, or shoulder replacement or other implanted article.

In one embodiment of the invention, the fluoroquinolone is directly injected into a wrinkle of a patient who has had cosmetic alteration of the wrinkle to prevent scar tissue formation.

As used herein, the terms "scar tissue" and "scar tissue formation" include any pathological condition resulting from fibrosis, including keloidosis, fibrocystic conditions and joint stiffness. The terms also include post-surgical adhesions or contractures, keloids, hyperplastic or hypertrophic masses formed following trauma, depressed scars from inflammatory responses including acne, wrinkling, cellulite formation, neoplastic fibrosis, and other fibrotic conditions involving fibroblast proliferation and metabolism at a localized area in the body. Such localized area may also be referred to herein as a site, situs or biological tissue. Therefore, the methods of the invention, which are directed to inhibiting fibroblast metabolism and proliferation, and more preferably to prevention and reduction of scar tissue formation, also contemplate treatment of conditions involving these pathologies.

Fluoroquinolones exhibit excellent gastrointestinal absorption, tissue penetration and a long half-life. (Bergeron, 1989; Zabraniecki et al., 1996). Thus, they exhibit excellent penetration into most organ systems, although they do not penetrate the blood-brain barrier. As a result, they have traditionally been indicated in a wide variety of infectious conditions, such as urinary tract, bronchopulmonary, and intestinal infections, as well as in the treatment of musculoskeletal infectious conditions such as septic arthritis and osteomyelitis. Side effects associated with the use of fluoroquinolones are rare but include musculoskeletal side effects. Many physicians have reported cases of rheumatologic conditions, including arthralgia, arthritis, tendinitis, and tendon rupture associated with the administration of ciprofloxacin. For example, hundreds of Achilles tendinitis and Achilles tendon rupture cases associated with fluoroquinolone therapy have been reported in the recent literature. (McGarvey et al., 1996;

Szarfman et al., 1995; Lee et al., 1992; de la Garza et al., 1997; Royer et al., 1994).

Although specimens from patients who suffered Achilles tendon rupture while taking ciprofloxacin have revealed irregular collagen fiber alignment (Movin et al., 1997), it is believed that the pathologic mechanism predisposing certain individuals to tendon injury has not been disclosed prior to this invention. Thus, the present invention relates, in part, to the determination of at least one mechanism for this pathology, and provides new uses for this class of drugs.

The present invention further provides surgical implants having one or more surfaces on which are coated or which otherwise contain a fluoroquinolone having an anti-fibrotic property and a pharmaceutically acceptable carrier. The carrier can be, e.g., a matrix, ointment, lavage, or gel.

Inhibitory fluoroquinolones for use in the invention include, without limitation, ciprofloxacin (Bayer, West Haven, Conn.), enoxacin (Rhone-Poulenc Rorer, Collegeville, Pa.), levofloxacin (Ortho McNeil Pharmaceutical, Raritan, N.J.), lomefloxacin (Searle, Chicago, Ill. and Unimed, Buffalo Grove, Ill.), norfloxacin (Merck & Co., West Point, Pa. and Roberts, Eatontown, N.J.), ofloxacin (Ortho McNeil Pharmaceutical) and sparfloxacin (Rhone-Poulenc Rorer). At suitable concentrations, fluoroquinolones inhibit fibroblast invasion or migration, even in the presence of suitable migration promoting substrates, such as laminin.

Inhibition of fibroblast cell proliferation and metabolism may be measured in vitro by analyzing collagen synthesis, PG synthesis and matrix metalloprotease, and is described in the Example, infra. Such methods are known generally in the art and can be used to assist in determination of an effective dosage for the particular fluoroquinolone employed in the method of the invention.

The methods of the present invention may further employ other therapeutically active compounds as noted herein which are usually applied in the treatment of the disclosed pathological conditions.

The phrase "pharmaceutically acceptable" refers to molecular entities and compositions that are physiologically tolerable when administered to a human and do not typically produce an allergic or similar untoward reaction, such as gastric upset, dizziness and the like. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans.

Pharmaceutically acceptable carriers include diluents, adjuvants, excipients, or vehicles with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution, saline solutions, and aqueous dextrose and glycerol solutions are preferably employed as carriers, particularly for injectable solutions. Suitable pharmaceutical carriers include those described in "Remington's Pharmaceutical Sciences" by E. W. Martin.

The phrase "therapeutically effective amount" as used herein means an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host, such as, in the present invention, the reduction or prevention of scar tissue formation, keloidosis, adhesions, pre-existing scars or wrinkles, acne scarring or hyper-normal scar formation, and the like. For example, in one embodiment, the method of the invention is employed to increase by a clinically significant amount the freedom of motion in a joint that has been subjected to orthopedic surgery, or which has been injured in a manner that normally results in generation of scar tissue that restricts motion.

As used herein, the term "about" or "approximately" means within 20 percent, preferably within 10 percent, and more preferably within 5 percent of a given value or range.

For oral administration, the compositions used are conventionally provided in the form of tablets containing from 100 to 1,000 milligrams of active ingredient depending on which fluroquinolone is selected. For intravenous, intralesional or parenteral administration, the compositions are preferably provided in vials or containers having 200 mg or 400 mg of active ingredient. The final dosage concentration can be symptomatically adjusted for any particular patient. Dosages are preferably administered on a regimen of 1 to 4 times per day, but can be increased as appropriately determined.

It will be understood, however, that the specific dosage level and frequency of administration for any particular patient may be varied and will depend upon a variety of factors including the activity of the specific compound employed, the metabolic stability and length of action of that compound, mode and time of administration, rate of excretion, drug combination, the severity of the particular condition, and the host undergoing therapy, including age, body weight, general health, sex, and diet. The methods of the present invention are suitable for treatment of animals, more preferably mammals, and most preferably humans.

The administration of a fluoroquinolone to reduce or prevent a condition described above may be accomplished using any mode of administration acceptable in the art two that makes it possible for the drug to access the situs requiring treatment. Such modes of administration may include oral, parenteral, intravenous, topical, cutaneous, subcutaneous, intramuscular, intranasal, intraocular, transdermal, etc. Preferably the mode of administration is systemic. Most preferably the mode of administration is oral or intravenous. Intrarticular injection may be used employing soluble fluoroquinolone agents. Intradermal injections may also be used.

Depending on the mode of administration the fluoroquinolone may require a particular formulation which includes additional excipients, fillers, buffers, etc. Such formulations are known and readily obtained by one skilled in the art. In most cases, fluoroquinolone formulations may be obtained from a pharmaceutical manufacturer such as Bayer, Inc., in ready to use dosages (e.g., tablets, I.V. bags, or vials). However, some formulations, such as those for intravenous or parenteral use, may require dilution or pH adjustment by one skilled in the art to achieve a physiologically acceptable dosage. These modifications will be appreciated by those skilled in the art. Thus, in using the present invention, a fluoroquinolone formulation may be adjusted for a particular mode of administration.

EXAMPLE 1

This Example demonstrates the inhibitory action of physiologic concentrations of the fluoroquinolone ciprofloxacin upon mammalian fibroblast metabolism and proliferation and matrix synthesis in vitro. It describes experiments in which both fibroblast proliferation and matrix synthesis were negatively affected by ciprofloxacin. An inhibitory effect was observed at concentrations of ciprofloxacin that can be attained in serum and tissues in human subjects following recoammended dosing regimens for this drug. The natural balance between anabolism and catabolism (i.e., tissue turnover), which exists in musculoskeletal tissues such as ligaments and tendons, is disrupted by ciprofloxacin. The inhibition of both fibroblast proliferation and the synthesis of matrix ground substance provides for novel methods of reducing scar tissue, and adhesions resulting from surgical procedures, using fluoroquinolone therapies according to methods of the invention.

Healthy, adult canine Achilles tendon, paratendon and shoulder capsule specimens were isolated and maintained in standard monolayer culture. Fibroblast cell cultures were incubated with 5 and 50 $\mu$g/ml of ciprofloxacin for analysis of cellular proliferation and 5, 10, and 50 $\mu$g/ml for analysis of matrix synthesis. Fibroblast proliferation, collagen synthesis ($^3$H-proline incorporation), PG synthesis ($^{35}$SO$_4$ incorporation), and matrix metalloprotease (collagenolytic) activity were also analyzed.

The use of canine cells in this Example is not intended to limit the invention, but rather to demonstrate the utility of the invention in mammals and more preferably in humans.

Methods

Isolation of tissue: Canine shoulder capsule, Achilles tendon and Achilles paratendon specimens were aseptically dissected from adult mongrel dogs, and soaked in M199 containing 10% antibiotic/antimycotic (ab/am) for 20 minutes. This process was repeated 3 times. Tissue was then minced into 1–2 mm cubes, and washed again in ab/am as described.

Cell culture: Minced tissue specimens were digested in 1% bacterial collagenase overnight and centrifuged. The digested tissue was suspended in M199 solution containing 10% ab/am. The cell suspension was centrifuged again, the supernatant removed, and the cellular pellet suspended in M199 containing 10% bovine fetal calf serum and 1% ab/am. Cells were then plated on T175 tissue culture flasks and grown almost to confluence. (Murrell et al., 1996).

Fibroblast culture: Pre-confluent monolayer cultures were treated with 0.25% trypsin in EDTA for approximately 5 minutes and then suspended in M199 complete. Isolated fibroblasts were plated on 12-well tissue culture plates at a density of $1\times10^4$ cells/well for conducting cellular proliferation studies or $1\times10^5$ cells/well for conducting matrix synthesis studies. Fibroblasts were maintained in culture for 24 hours to promote cellular adhesion. Fibroblast cell cultures were maintained with M199 complete solution (minimum n=4). The fluoroquinolone antibiotic, 1-cyclopropyl-6-fluoro-1,4-dihydro-4-oxo-7-(1-piperazinyl)-3-quinolinecarboxylic acid (ciprofloxacin) (Bayer) was added to experimental cell culture in the following concentrations: 5 µg/ml, 10 µg/ml, and 50 µg/ml. These concentrations represent the range of values observed in humans following intravenous or oral administration of ciprofloxacin according to the Physician's Desk Reference. Control wells for each plate were maintained with M199 complete alone. Medium was changed every 48 hours for all cultures.

Cellular proliferation: In vitro fibroblast proliferation was determined by counting cells using a Coulter counter. Cell counts were performed every 24 hours beginning with day 2 through day 4 following co-incubation with ciprofloxacin at 5 and 50 µg/ml.

Matrix synthesis: In vitro collagen synthesis was measured by incorporation of $^3$H-Proline. Isolated cells were incubated for 24 hours at day 4–5 in M199 complete supplemented with 25 µg/ml ascorbic acid and labeled with 10 µg/ml $^3$H-Proline in the presence of ciprofloxacin at 5, 10, and 50 µg/ml. Control cells were not challenged with ciprofloxacin.

In vitro fibroblast PG synthesis was assessed by incorporation of $^{35}SO_4$. Isolated cells were incubated for 24 hours in M199 complete supplemented with 25 µg/ml ascorbic acid and labeled with 10 µg/ml $^{35}SO_4$ (at day 4–5) in the presence of ciprofloxacin at 5, 10, or 50 µg/ml. Control cells were not challenged with ciprofloxacin.

After incubation, the cell associated fraction of cultured fibroblasts cells were harvested using cold phosphate buffered saline wash (2x), methanol wash (2x), and distilled $H_2O$ wash (5x). Cells were then dissolved in 0.3 N NaOH, and suspended in scintillation cocktail. Radioactivity (dpm) was determined using a scintillation counter.

Cell viability: Cell respiration, an indicator of cell viability, was assessed by the mitochondrial-dependent reduction of 3-(4,5-dimethylthiazol-2-yl)-2,5-diphenyltetrazolium bromide (MTT) to formazan as described in Williams et al. 1991. In addition, cell viability was assessed using Trypan blue dye exclusion according to standard protocols in the art.

Matrix degrading activity: Medium from shoulder capsule, Achilles tendon, and Achilles paratendon cells co-incubated with 5, 10 and 50 µg/ml ciprofloxacin was analyzed for matrix metalloprotease (caseinoltyic) activity. Medium from control cultures was also analyzed for proteolytic activity using the substrate assays described in Williams et al., 1991.

Results

Fibroblast proliferation: Incubation of isolated Achilles tendon, Achilles paratendon and shoulder capsule fibroblasts with ciprofloxacin at 5 or 50 µg/ml resulted in a significant decrease in cellular proliferation as compared with control cells at 48 and 72 hours in culture ($p<0.05$).

Collagen synthesis: Ciprofloxacin at 50 µg/ml caused a significant decrease in the incorporation of $^3$H-Proline into Achilles tendon, Achilles paratendon, and shoulder capsule cells as compared with controls ($p<0.05$). Collagen synthesis was inhibited 38%, 48%, and 36% in Achilles tendon, Achilles paratendon, and shoulder capsule fibroblasts, respectively. No significant differences in $^3$H-proline incorporation were noted in cultures treated with 5 µg/ml or 10 µg/ml ciprofloxacin as compared with unstimulated control cultures.

Proteoglycan synthesis: Ciprofloxacin inhibited PG synthesis in Achilles tendon and Achilles paratendon fibroblast cultures, as measured by the incorporation of $^{35}SO_4$, in a dose dependent fashion). Ciprofloxacin at 5 µg/ml inhibited Achilles tendon PG synthesis by 14%, which was not statistically significant. However, ciprofloxacin at concentrations of 10 and 50 µg/ml decreased sulfate incorporation into Achilles tendon cells by 19% and 55%, respectively, which was statistically significant ($p<0.05$). Achilles paratendon cells incubated with 5, 10, and 50 µg/ml ciprofloxacin showed statistically significant ($p<0.05$) decreases in sulfate incorporation of 18%, 26%, and 51%, respectively. Shoulder capsule fibroblast $^{35}SO_4$ incorporation was inhibited 60% with 50 µg/ml of ciprofloxacin ($p<0.05$), but at lower ciprofloxacin concentrations, e.g., 5 µg/ml, the inhibitory effect was not observed.

Matrix degrading activity: A significant increase in metalloprotease (caseinolytic) activity was observed in culture medium from Achilles tendon, paratendon and shoulder capsule fibroblasts incubated with ciprofloxacin at 5, 10, and 50 µg/ml over a 72 hour interval (44%–150% increase in caseinolytic activity) ($p<0.05$).

Cell viability: All fibroblast cell cultures remained viable after incubation with ciprofloxacin at concentrations of 5, 10, and 50 µg/ml.

Discussion

The present Example demonstrates that the fluoroquinolone antibiotic ciprofloxacin has a direct inhibitory effect upon fibroblast metabolism as measured by cellular proliferation, collagen synthesis, PG synthesis, and matrix synthesis at physiologic levels. This inhibitory effect was demonstrated in three separate fibroblast populations, including Achilles tendon, Achilles paratendon and shoulder capsule cells. At increasing concentrations of ciprofloxacin, ranging from 5–50 µg/ml, there is increased inhibition of fibroblast metabolism. Typical serum concentrations of ciprofloxacin following oral and intravenous administration ranges between 0.5–10 µg/ml. (Bergeron 1989; Shah et al., 1994; Crump et al., 1983; MacGowan et al., 1994). While the most profound inhibitory effects are observed at higher concentrations of ciprofloxacin, statistically significant inhibition of both fibroblast proliferation and matrix synthesis was observed at concentrations usually detected in serum after standard oral and intravenous dosing regimens given by physicians, e.g., from 5 to 50 µg/ml.

The inhibitory activity of ciprofloxacin on fibroblast metabolism is evident in a variety of cellular processes. For instance, at low concentrations, ciprofloxacin increased caseinolytic activity (proteoglycanase), which was observed in all three fibroblast populations tested. It also reduced PG and matrix molecule syntheses (i.e., collagen and PG), which are consequences of fibroblast metabolism. The combination of increased local metalloprotease activity and decreased ground substance production of fibroblasts caused by fluoroquinolones now explains the occurrence of tendinitis and tendon rupture in certain individuals treated with fluoroquinolone antibiotics.

Without wishing to be bound by any theory related to the invention, the metalloprotease activity of fibroblasts in vivo may cause damage to the extracellular matrix and result in weakening of a tendon and causing it to rupture. Since local increases in matrix degrading protease predispose affected tendons to injury, it appears that ciprofloxacin not only inhibits fibroblast metabolism, but also stimulates fibroblast-derived metalloprotease activity. Therefore, fluoroquinolones at concentrations attainable in vivo can inhibit fibroblast matrix synthesis and proliferation in vitro. According to the invention, they are used to treat pathologic responses involving increased fibroblast metabolism and proliferation, such as formation of scar tissue and adhesions, and the like.

EXAMPLE 2

A second fluoroquinolone drug, ofloxacin, was tested as described above using the same three fibroblast cell lines, ie., Achilles tendon, paratendon and shoulder capsule. The observed inhibition of proliferation and proline and sulfate incorporation was less than that observed for ciprofloxacin, but was nevertheless significant compared to unstimulated control fibroblasts.

EXAMPLE 3

To inhibit the formation of scar tissue in a patient who will undergo shoulder surgery, ciprofloxacin is administered in a dosage of 250 to 1000 mg, per a day, for a period of 1 to 3 days prior to the surgery. Following the surgery, ciprofloxacin is administered in a dosage of 500–750 mg/ml during the first 6 hours following surgery. Administration of ciprofloxacin is continued for 1 to 4 weeks at a dosage from 250 to 750 mg two times a day. The dosage may be decreased to 250 mg/day after 4 weeks, following the surgery. After 6 weeks following surgery, treatment is completed and scar tissue formation is inhibited, thus resulting in increased shoulder range of motion.

REFERENCES

1. Bergeron M. The pharmacokinetics and tissue penetration of the fluoroquinolones. Clin Invest Med 1989; 12:20–27.
2. Zabraniecki L, Negrier I, Vergne P, et al. Fluoroquinolone induced tendinopathy: Report of 6 cases. J Rheumatol 1996; 23:516–20.
3. McGarvey W, Singh D, Trevino S. Partial Achilles tendon ruptures associated with fluoroquinolone antibiotics: A case report and literature review. Foot & Ankle International 1996; 17:496–98.
4. Szarfman A, Chen M, Blum M. More on fluoroquinolone antibiotics and tendon rupture. N Eng J Med 1995; 332:193.
5. Lee W, Collins J. Ciprofloxacin associated bilateral Achilles tendon rupture. Aust N Z J Med 1992; 22:500.
6. de la Garza Estrada V, Vazquez Caballero .R, Camacho Carranza J. Achilles tendon rupture and fluoroquinolones use: report of two cases. Arch Med Res 1997; 28:429–30.
7. Royer R, Pierfitte C, Pierfitte N, Features of tendon disorders with fluoroquitiolones. Therapie 1994; 49:75–76.
8. Movin T, Gad A, Gunter P, Foldhazy Z, Rolf C. Pathology of Achilles tendon in association with ciprofloxacin treatment, Foot & Ankle International 1997; 18:297–99.
9. Murrell G A, Dolan M, Jang D, Szabo C, Warren R F, Hannafm J A. Nitric oxide: an important articular free radical. J Bone Joint Surg 1996; 78:265–74.
10. Shah A, Lettieri J, Kaiser L, Echols R, Heller A. Comparative pharmocokinctics and safety of ciprofloxacin 400 mg iv thrice daily versus 750 mg po tice daily. Journal of Antimicrobial Chemotherapy 1994; 33;795–801.
11. Crump B, Wise R, Dent J. Pharmacokinetics and tissue penetration of ciprofloxacin. Antimicrob Agents Chemother 1983; 24:784–86.
12. MacGowan A, White L, Brown N, Lovering A, McMullin C, Reeves D. Senim ciprofloxacin concentrations in patients with severe sepsis being treated with ciprofloxacin 200 mg iv bd irrespective of renal function. Journal of Antimicrobial Chemotherapy 1994; 33:1051–54.
13. Williams R J 3d, Smith R L, Schurman D J. Purified staphylococcal culture medium stimulates neutral metalloprotease secretion from human articular cartilage. J Orthop Res 1991 Mar;9(2):258–65.

What is claimed is:

1. A surgical implant having a surface comprising an antifibrotic effective amount of a fluoroquinolone and a carrier, wherein said surface is coated with or otherwise contains the fluoroquinolone.

2. The implant of claim 1, wherein said carrier is selected from the group consisting of a matrix, ointment, lavage, and gel.

3. The implant of claim 1, wherein the fluoroquinolone is selected from the group consisting of ciprofloxacin, enoxacin, levofloxacin, lomefloxacin, norfloxacin, ofloxacin, pefloxacin, and sparfloxacin.

4. The implant of claim 1 wherein the fluoroquinolone is ciprofloxacin.

5. The implant of claim 1 comprising an orthopedic implant.

6. A method for inhibiting fibrosis in a mammal comprising the step of contacting a therapeutically effective amount of a fluoroquinolone with a biological tissue of said mammal in need of such inhibition.

7. A method for inhibiting fibroblast proliferation, fibroblast metabolism, collagen synthesis, proteoglycan synthesis, or matrix synthesis in a mammal comprising the step of contacting a biological tissue of said mammal in need of such inhibition with a therapeutically effective amount of a fluoroquinolone.

8. A method for treating scar tissue formation, keloidosis, joint stiffness, or fibrocystic condition in a mammal in need of such treatment comprising the step of administering to said mammal a composition comprising a pharmaceutically effective amount of a fluoroquinolone and a pharmaceutically acceptable carrier.

9. The method according to claim 6 wherein the tissue is a pre-existing scar or a pre-existing keloid.

10. The method according to claim 6 comprising inhibiting formation of scar tissue resulting from a surgical procedure.

11. The method according to claim 6 wherein the mammal is a human or domesticated animal.

12. The method according to claim 6 wherein the fluoroquinolone is contacted with said tissue in a concentration of from about 0.1 µg/ml to about 100 µg/ml.

13. The method according to claim 6 wherein the amount of fluoroquinolone is contacted with said tissue in a concentration of from about 5 µg/ml to about 50 µg/ml.

14. The method according to claim 6 wherein the fluoroquinolone is contacted with said tissue for a period of from about 1 day to about 6 weeks.

15. The method according to claim 6 wherein the fluoroquinolone is administered before a surgical procedure.

16. The method according to claim 6 wherein the fluoroquinolone is selected from the group consisting of ciprofloxacin, enoxacin, levofloxacin, lomefloxacin, norfloxacin, ofloxacin, pefloxacin, and sparfloxacin.

17. The method according to claim 6 wherein the lesion or scar tissue is selected from the group consisting of an adhesion, joint capsule contracture, surgical lesion, traumatic injury, non-topical wound, topical wound, acne, and a hypertrophic scar.

18. The method according to claim 6 wherein the fluoroquinolone is administered by a means selected from the group consisting of intra-lesionally, pharmaceutically acceptable surgical implantion, orally, intravenously, intrarticularly, intradermally, and parenterally.

19. A method for inhibiting fibrosis in a patient who has had cosmetic alteration of a preexisting wrinkle or wrinkles comprising the step of administering a pharmaceutically effective amount of a fluoroquinolone and a pharmaceutically acceptable carrier directly into said wrinkle or wrinkles.

20. The method of claim 19, wherein the fibrosis comprises the formation of scar tissue.

21. The method of claim 20, wherein the formation of scar tissue comprises the formation of wrinkles.

* * * * *